(12) United States Patent
Wong

(10) Patent No.: US 7,440,099 B2
(45) Date of Patent: Oct. 21, 2008

(54) DROPLETS DETECTING SYSTEM

(75) Inventor: Ren-Sue Wong, Sunnyvale, CA (US)

(73) Assignee: ICF Technology Limited, Santa Clara ( * ) Notice: Subject to any disclaimer, the term of this patent is extended or adjusted under 35 U.S.C. 154(b) by 17 days.

(21) Appl. No.: 11/309,500

(22) Filed: Aug. 14, 2006

(65) Prior Publication Data

US 2008/0037016 A1 Feb. 14, 2008

(51) Int. Cl.
*G01N 15/02* (2006.01)
(52) U.S. Cl. .................. 356/335; 356/432; 356/436; 347/6; 347/14
(58) Field of Classification Search .......... 356/335, 356/432–436; 347/6–14
See application file for complete search history.

(56) References Cited

U.S. PATENT DOCUMENTS 4,328,504 A * 5/1982 Weber et al. ................. 347/14
4,493,993 A 1/1985 Kanamuller et al.
4,778,593 A * 10/1988 Yamashita et al. ............ 356/39
6,357,849 B2 * 3/2002 Takizawa et al. ............. 347/19

* cited by examiner

*Primary Examiner*—L. G. Lauchman
*Assistant Examiner*—Iyabo S Alli
(74) *Attorney, Agent, or Firm*—Andrew C. Cheng

(57) ABSTRACT

A droplets detecting system (100) includes a laser diode assembly (20), a photo diode (30), a light source (40), a charge coupled device camera (50), a signal processing and displaying device (32), and an image processing and displaying device (52). The laser diode assembly is configured for emitting a laser light (26) to pass through a droplet (204). The photo diode is configured for receiving the laser light passing through the droplet and for generating an electronic signal. The light source is configured for emitting an illuminating light (42) to illuminate the droplet. The charge coupled device camera is configured for receiving the illuminating light and photographing the illuminated droplet. The signal processing and displaying device is connected with the photo diode and is configured for displaying the electronic signal generated by the photo diode. The image processing and displaying device is connected with the charge coupled device camera.

15 Claims, 13 Drawing Sheets

DROPLETS DETECTING SYSTEM

FIELD OF THE INVENTION

The present invention relates to a detecting system for detecting droplets jetted from a nozzle such as an ink-jet nozzle.

DESCRIPTION OF RELATED ART

A liquid crystal display typically utilizes a color filter to display images and graphs. The color filter is constructed by arranging colored portions colored in red (R), green (G), and blue (B), as three primary colors of light on a transparent substrate. A dyeing method, a pigment dispersing method, and an electrodepositing method, etc. are generally used as manufacturing methods for the color filter. Recently, an ink jet system, simple in process and economically advantageous, has been used.

The ink jet system mainly includes one or more print heads. Each print head has a plurality of ink-jet nozzles. The print head can make the ink-jet nozzles jet R, G, or B ink droplets onto the transparent substrate to form a corresponding colored portion. A jetting condition of each ink-jet nozzle needs to be determined via detecting droplet characteristics such as shape, frequency, size, absence/presence, directionality, and so on, so that the ink jet system can be timely adjusted before use.

What is needed, therefore, is a detecting system that can detect droplets jetted from a nozzle.

SUMMARY OF THE INVENTION

A droplets detecting system according to one preferred embodiment includes a laser diode assembly, a photo diode, a light source, a charge coupled device camera, a signal processing and displaying device, and an image processing and displaying device. The laser diode assembly is configured (i.e., structured and arranged) for emitting a laser light to pass through a droplet. The photo diode is configured (i.e., structured and arranged) for receiving the laser light passing through the droplet and for thereby generating an electronic signal. The light source is structured and arranged for emitting an illuminating light to illuminate the droplet. The charge coupled device camera is configured (i.e., structured and arranged) for receiving the illuminating light and thereby photographing the illuminated droplet. The signal processing and displaying device is connected with the photo diode and is configured (i.e., structured and arranged) for displaying the electronic signal generated by the photo diode. The image processing and displaying device is operatively connected with the charge coupled device camera and is configured (i.e., structured and arranged) for displaying enlarged image of the droplet.

Other advantages and novel features will become more apparent from the following detailed description of present droplets detecting system, when taken in conjunction with the accompanying drawings.

BRIEF DESCRIPTION OF THE DRAWINGS

Many aspects of the present droplets detecting system can be better understood with reference to the following drawings. The components in the drawings are not necessarily to scale, the emphasis instead being placed upon clearly illustrating the principles of the present droplets detecting system. Moreover, in the drawings, like reference numerals designate corresponding parts throughout the several views.

FIGS. 3A and 3B are an image and a graph displayed by the droplets detecting system of FIG. 1, wherein the print head is in a first jetting condition;

FIGS. 5A and 5B are an image and a graph displayed by the droplets detecting system of FIG. 1, wherein the print head is in a third jetting condition;

DETAILED DESCRIPTION OF THE INVENTION

Reference will now be made to the drawings to describe preferred embodiment of the present droplets detecting system, in detail.

Figure 1:
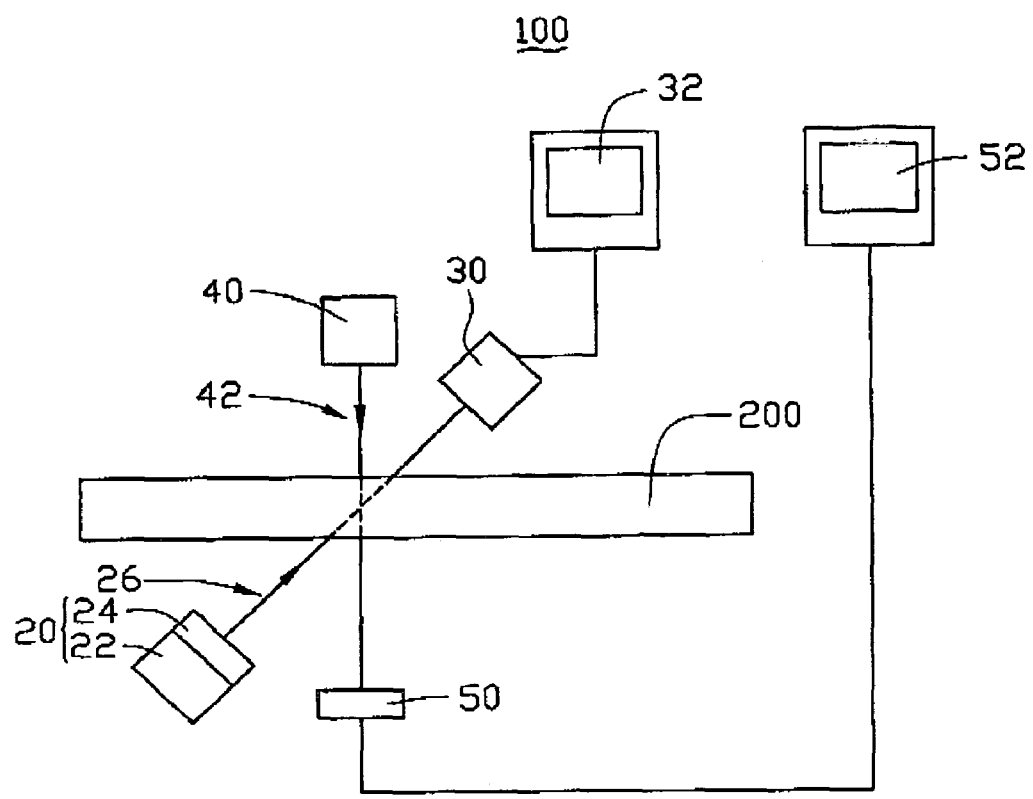
FIG. 1 is a schematic, plan view of a droplets detecting system and a print head, in accordance with a first embodiment.
Figure 2:
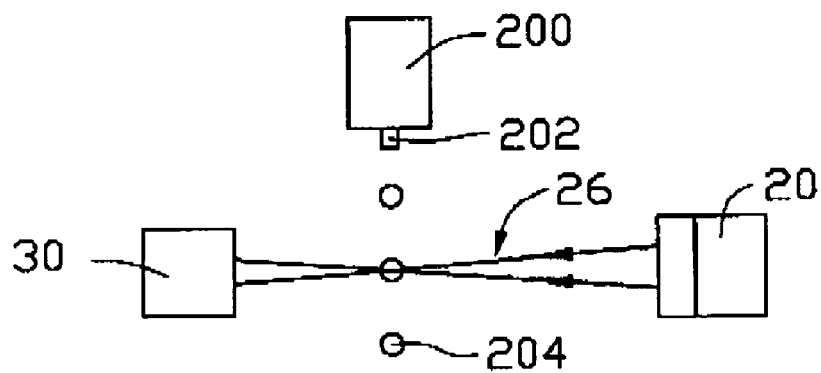
FIG. 2 is a schematic, side view of the print head, a laser assembly and a photo diode of the droplets detecting system of FIG. 1.
Figure 3B:
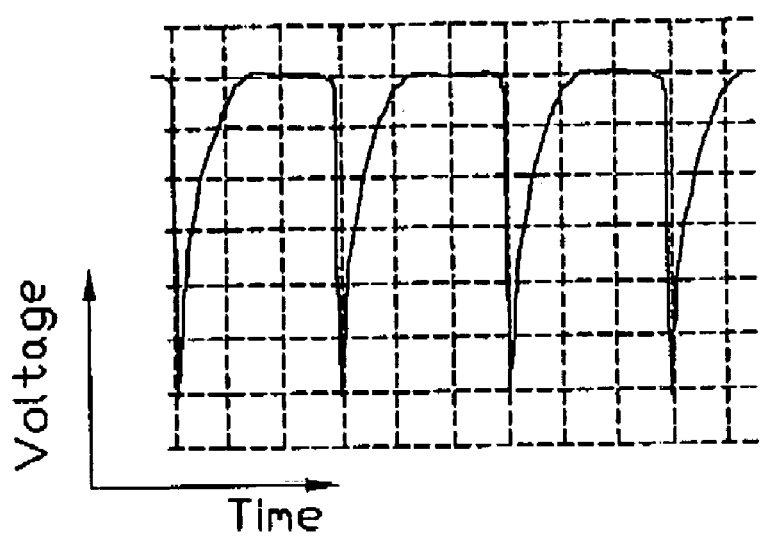
Figure 4A:
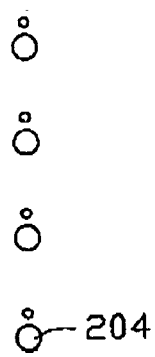
FIGS. 4A and 4B are an image and a graph displayed by the droplets detecting system of FIG. 1, wherein the print head is in a second jetting condition.
Figure 4B:
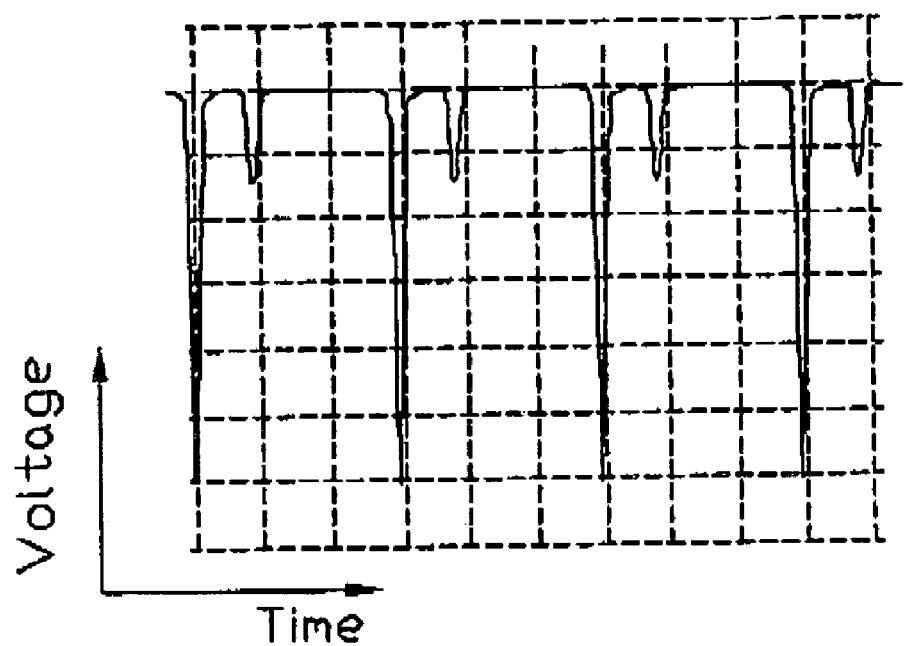
Figure 5B:
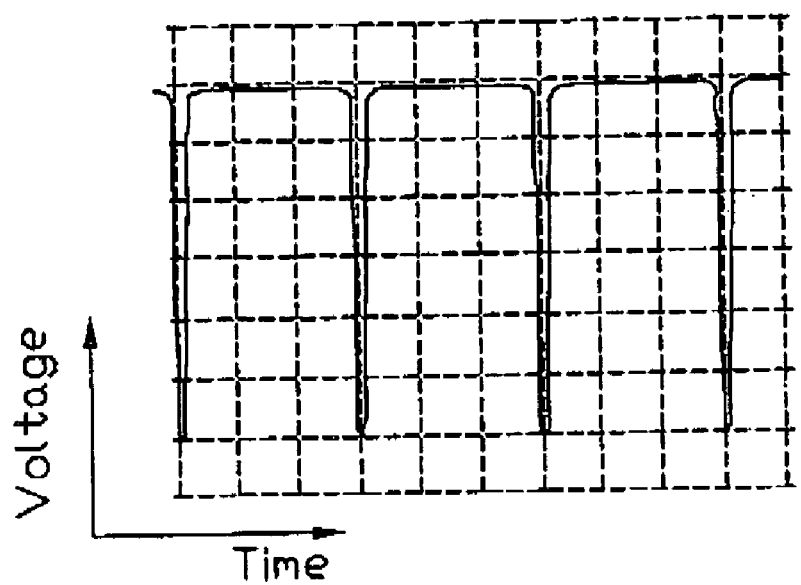

Referring to FIGS. 1 and 2, a droplets detecting system 100, in accordance with a first embodiment, is shown. The droplets detecting system 100 includes a laser diode assembly 20, a photo diode 30, a signal processing and displaying device 32, a light source 40, a charge coupled device (CCD)) camera 50, and an image processing and displaying device 52. The laser diode assembly 20 faces towards the photo diode 30, and the photo diode 30 operatively links with one input port of the signal processing and displaying device 32. The light source 40 faces towards the CCD camera 50, and the CCD camera 50 connects with the image processing and displaying device 52. The laser diode assembly 20 and the light source 40 are arranged in a manner to illuminate a droplet 204, jetted from an ink-jet nozzle 202, in different directions.

Specifically, the laser diode assembly 20 includes a laser diode 22 and a lens module 24. The laser diode 22 can emit a laser light 26, and the lens module 24 can be used to focus the laser light 26 onto a desirable spot under one ink-jet nozzle 202 of a print head 200 so that the focused laser light 26 can pass through droplets 204 jetted from the ink-jet nozzle 202. Preferably, the focused spot of the laser light 26 has a size smaller than that of the droplet 204. The light source 40 and the photo diode 30 are located at the same side of the print head 200. The photo diode 30 can receive the laser light 26 passing through the droplet 204 and generate a corresponding electronic signal. In the preferred embodiment, the signal processing and displaying device 32 is an oscilloscope capable of displaying the electronic signal generated by the photo diode 30. Alternatively, an analog-digital conversion board with software can also be used as the signal processing and displaying device 32.

The light source 40 can, advantageously, be a light emitting diode. A switching frequency of the light source 40 is synchronized with a jetting frequency of the ink-jet nozzle 202 so that the light source 40 can emit an illuminating light 42 to illuminate each droplet 204, and the CCD camera 50 can photograph an image of each droplet 204. The image processing and displaying device 52 includes a monitor adapted/designed for displaying the image of the droplets 204 photographed by the CCD camera 50.

The droplets detecting system 100 can be used for detecting droplets 204 jetted from the ink-jet nozzles 202 set on the print head 200 so that a jetting condition of each ink-jet nozzle 202 can be determined. Following are detailed descriptions on detecting process employing the droplets detecting system 100.

Referring to FIGS. 1 to 3B, in a first jetting condition of the ink-jet nozzles 202, the print head 200 is kept immobile and elongate round droplets are jetted from one nozzle 202. Under this condition, the CCD camera 50 can photograph the illuminated droplets 204, and a photographed image of the illuminated droplets 204 is displayed on the monitor of the image processing and displaying device 52 (referring to FIG. 3A). Because the image is enlarged, the shape of the droplets can be conveniently detected. At the same time, the laser light 26 passes through the moving droplets 204 and is incident upon the photo diode 30. The photo diode 30 receives the light signal of the laser light 26 and generates a corresponding electronic signal. The signal processing and displaying device 32 displays the electronic signal against time and aids the detection of the droplets 204 (referring to FIG. 3B). Because the droplets 204 can absorb a portion of the laser light 26 and an absorbed amount is different according to different parts of the droplets 204, the electronic signal displayed on the signal processing and displaying device 32 can express the shape of the droplets 204, such as a low voltage can represent a large diameter of the droplet 204. Other characters of the droplets 204 such as frequency, rate and size can also be calculated by known methods via the signal processing and displaying device 32. Similarly, after moving the print head 200 and making the other ink-jet nozzles 202 respectively above the light path of the droplets detecting system 100, the other ink-jet nozzles 202 can also be tested.

Figure 6A:
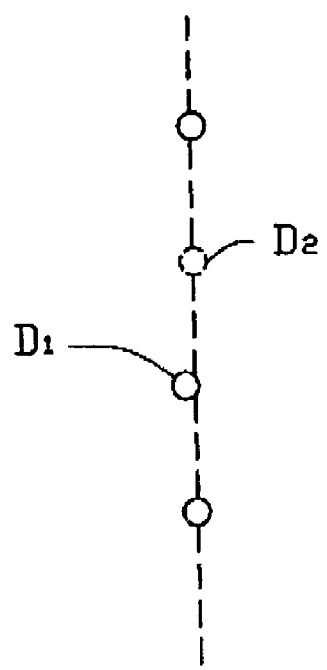
FIGS. 6A and 6B are an image and a graph displayed by the droplets detecting system of FIG. 1, wherein the print head is in a fourth jetting condition.
Figure 6B:
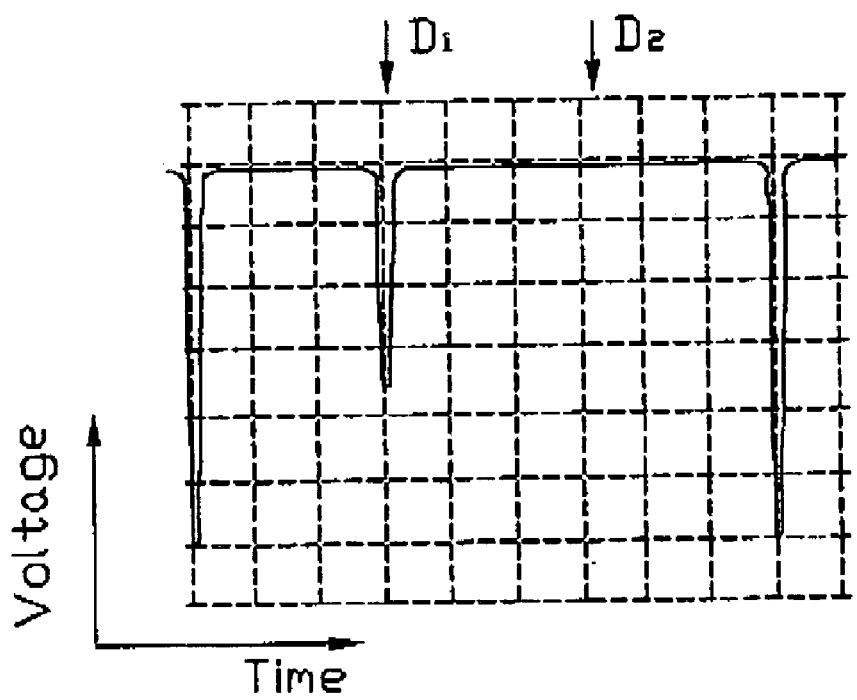

Referring to FIGS. 4A to 6B, in other jetting conditions of the ink-jet nozzles 202, the images and graphs can be similarly displayed by the droplets detecting system 100. Particularly, as shown in FIGS. 6A and 6B, a droplet $D_1$ having a bad directionality and a missing droplet $D_2$ can also be detected by the droplets detecting system 100. A decreased signal of droplet $D_1$ shows that the nozzle 202 is in a bad stability.

Figure 7:
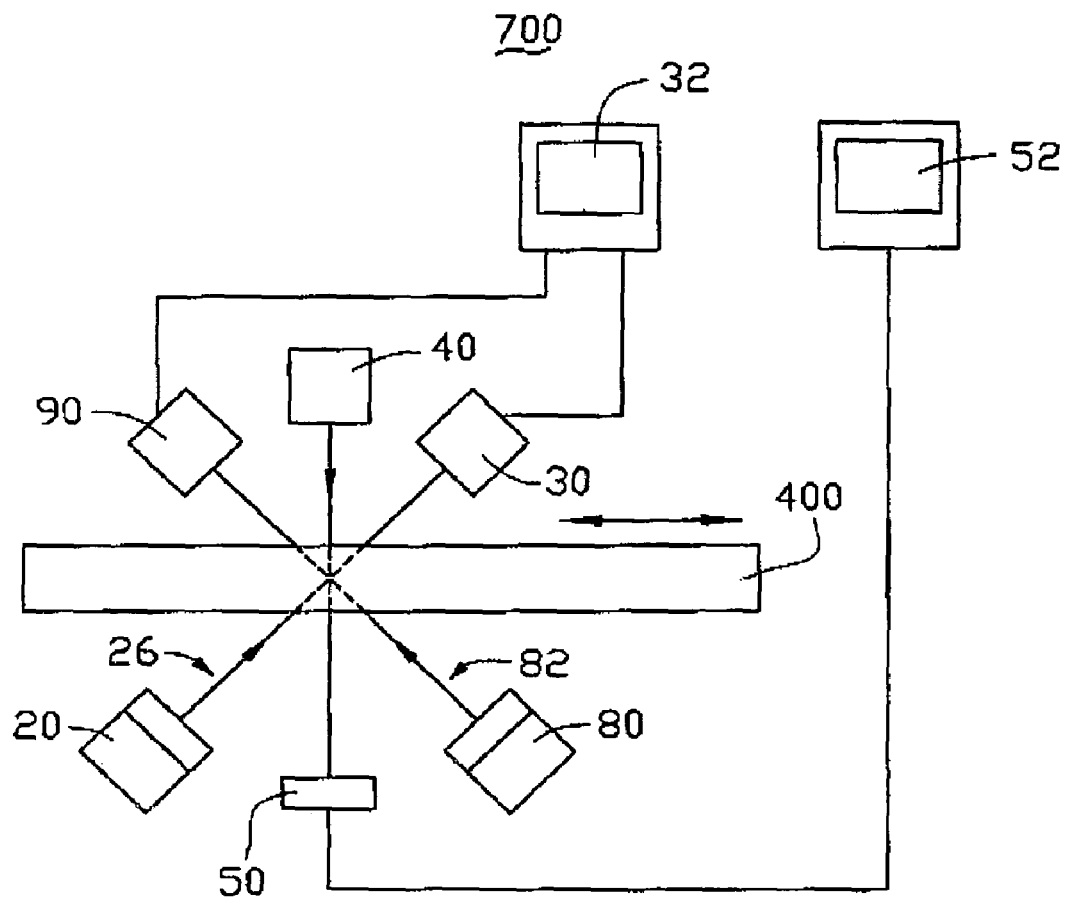
FIG. 7 is a schematic, plan view of a droplets detecting system and a print head, in accordance with a second embodiment.

Referring to FIG. 7, a droplets detecting system 700, in accordance with a second embodiment, is shown. The detecting system 700 is similar to the droplets detecting system 100 of the first embodiment. The difference is that the droplets detecting system 700 further includes a laser diode assembly 80 similarly to the laser diode assembly 20, and a photo diode 90 similarly to the photo diode 30. The laser diode assembly 80 faces towards the photo diode 90, and the photo diode 90 operatively links with another input port of the signal processing and displaying device 32. The laser diode assembly 80 can generate a focused laser light 82, and the focus of the focused laser light 82 is similar to the focus of the laser light 26. The laser diode assembly 20, the laser diode assembly 80 and the light source 40 are arranged in a manner to illuminate the droplet in different directions.

Figure 8A:
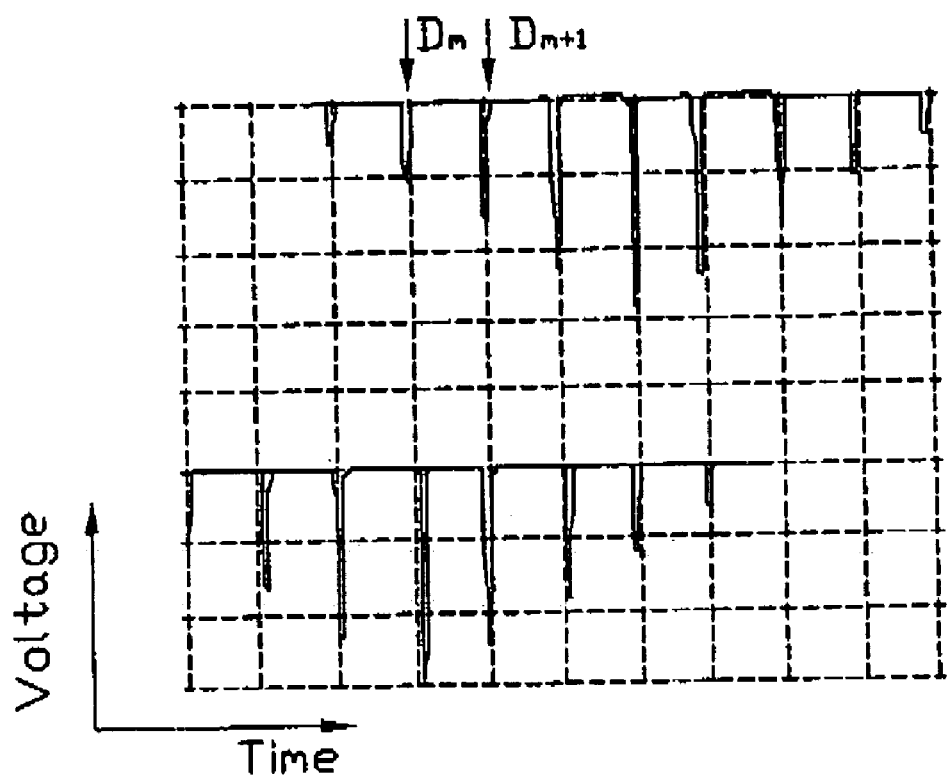
FIG. 8A is a voltage over time graph displayed by the droplets detecting system of FIG. 7, wherein the print head is in a first jetting condition.
Figure 8B:
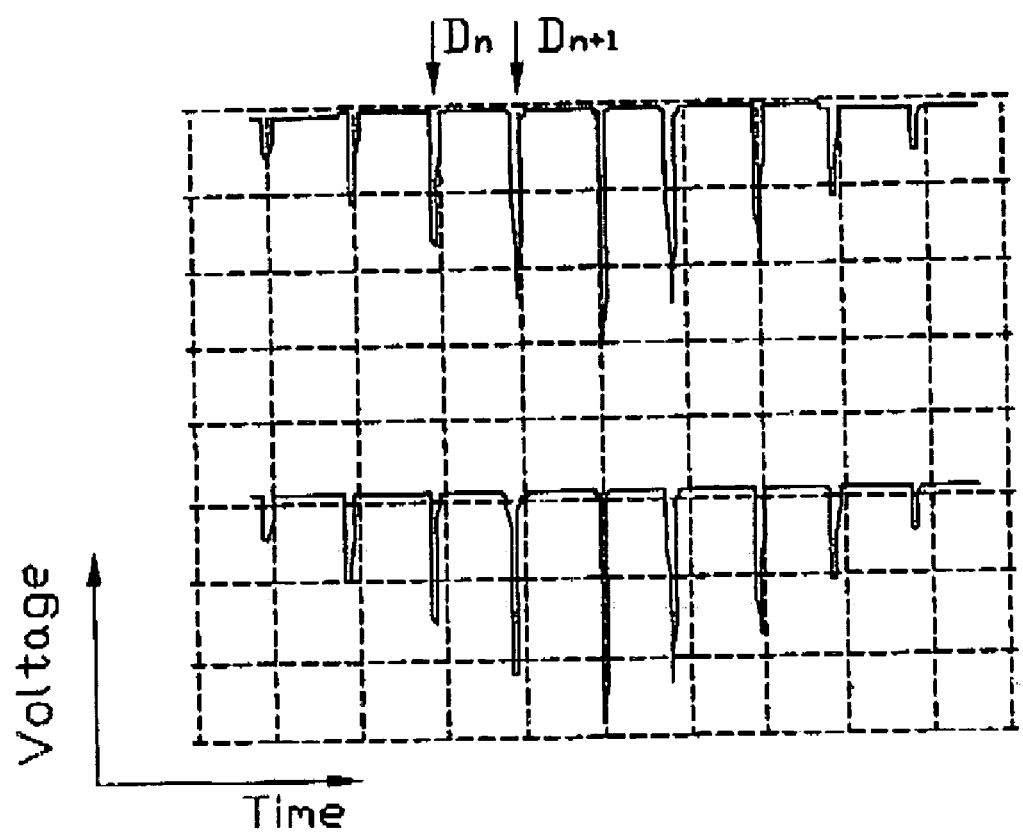
FIG. 8B is a voltage over time graph displayed by the droplets detecting system of FIG. 7, wherein the print head is in a second jetting condition.

Under this configuration, the droplets detecting system 700 can achieve the functions of the droplets detecting system 100, and further detect directionality of a moving print head 400 similarly to the print head 200. Referring to FIGS. 7 and 8A, when the print head 400 moves along either of arrow directions and the directionality of the print head 400 is not perfect, such as the print head 400 is inclining, the droplets such as $D_m$, $D_{m+1}$ cannot block the laser light 26 and 82 at the same time. Thus, intensities of two corresponding electronic signals generated by the two photo diodes 30 and 90 are different, and the print head 400 needs to be further checked and adjusted for use. Referring to FIGS. 7 and 8B, when the print head 400 moves along either of the arrow directions and the directionality of the print head 400 is perfect, the droplets such as $D_n$, $D_{n+1}$ can block the laser light 26 and 82 at the same time. Thus, intensities of two corresponding electronic signals generated by the two photo diodes 30 and 90 are same.

It is to be understood that the above-described embodiment is intended to illustrate rather than limit the invention. Variations may be made to the embodiment without departing from the spirit of the invention as claimed. The above-described embodiments are intended to illustrate the scope of the invention and not restrict the scope of the invention.

What is claimed is:

1. A droplets detecting system configured for detecting droplets jetted out from a same ink-jet nozzle, comprising:
    a first laser diode assembly configured for emitting a first laser light to pass through the droplet, the first laser diode assembly being immoveable relative to the ink-jet nozzle;
    a first photo diode configured for receiving the first laser light passing through each droplet and for thereby generating a first electronic signal;
    a light source structured and arranged for emitting an illuminating light to illuminate the droplet passed through by the first laser light, wherein the first laser diode assembly and the light source are arranged in a manner to illuminate the droplet from different directions;
    a charge coupled device camera configured for receiving the illuminating light and thereby photographing the illuminated droplet;
    a signal processing and displaying device connected with the first photo diode, the signal processing and displaying device being configured for displaying the first electronic signal generated by the first photo diode; and
    an image processing and displaying device operatively connected with the charge coupled device camera, the image processing and displaying device being configured for displaying an enlarged image of the droplet.

2. The droplets detecting system as claimed in claim 1, wherein the first laser diode assembly comprises a first laser diode configured for emitting the first laser light and a first lens module configured for focusing the first laser light on a first desirable spot.

3. The droplets detecting system as claimed in claim 2, wherein the signal processing and displaying device is an oscilloscope.

4. The droplets detecting system as claimed in claim 3, wherein the oscilloscope comprises two input ports, the oscilloscope being connected with the first photo diode through one input port.

5. The droplets detecting system as claimed in claim 4, further comprising:
    a second laser diode assembly configured for emitting a second laser light to pass through the droplet; and
    a second photo diode configured for receiving the second laser light passing through the droplet and for generating a second electronic signal;
    wherein the first laser diode assembly, the second laser diode assembly and the light source are arranged in a manner to illuminate the droplet from different directions, the second laser light being focused on the first desirable spot, the oscilloscope being connected with the second photo diode through another input port and being configured for displaying the second electronic signal generated by the second photo diode.

6. The droplets detecting system as claimed in claim 5, wherein the second laser diode assembly comprises a second laser diode and a second lens module being used to focus the second laser light on the first desirable spot.

7. The droplets detecting system as claimed in claim 1, wherein the signal processing and displaying device is an analog-digital conversion board with software.

8. The droplets detecting system as claimed in claim 1, wherein the light source is a light-emitting diode.

9. The droplets detecting system as claimed in claim 1, wherein the signal processing and displaying device is an oscilloscope.

10. A droplets detecting system for detecting droplets jetted from a same ink-jet nozzle, comprising:
   a laser diode assembly configured for providing a laser light which focuses to a spot through which the droplets, jetted out from the ink-jet nozzle, pass sequentially;
   an illuminating device configured for illuminating the droplets when the droplets pass through the spot, wherein the laser diode assembly and the illuminating device are arranged in a manner to illuminate each droplet from different directions;
   a photographing assembly configured for photographing the illuminated droplets and displaying enlarged images of the illuminated droplets; and
   a signal processing and displaying assembly facing toward the laser diode assembly and configured for receiving the laser light passing through the droplets and displaying an electronic signal transferred from the received laser light.

11. The droplets detecting system as claimed in claim 10, wherein the laser diode assembly comprises a laser diode configured for emitting the laser light, and a lens module configured for focusing the laser light to the spot.

12. The droplets detecting system as claimed in claim 10, wherein the photographing assembly comprises a camera configured for photographing the illuminated droplets, and an image processing and displaying device connected with the camera and configured for displaying the enlarged image of the illuminated droplets.

13. The droplets detecting system as claimed in claim 10, wherein the signal processing and displaying assembly comprises a photo diode configured for receiving the laser light to generate the electronic signal, and a signal processing and displaying device connected with the photo diode and configured for displaying the electronic signal.

14. The droplets detecting system as claimed in claim 13, further comprising an additional laser diode assembly configured for providing an additional laser light which focuses to the spot, an additional photo diode connected with the signal processing and displaying device and configured for receiving the additional laser light and transmitting to the signal processing and displaying device an additional electronic signal transferred from the additional laser light.

15. The droplets detecting system as claimed in claim 1, wherein a switching frequency of the light source is synchronized with a jetting frequency of the ink-jet nozzle.

* * * * *